United States Patent
Dabholkar et al.

(10) Patent No.: US 7,476,394 B2
(45) Date of Patent: Jan. 13, 2009

(54) DETERGENT COMPOSITION WITH BENEFIT AGENTS

(75) Inventors: Nandini Sachin Dabholkar, Mumbai (IN); Venkareswaran Krishnan, Bangalore (IN); Pankaj Chandrakant Shah, Mumbai (IN); Ananthasubramanian Sivakumar, Mumbai (IN)

(73) Assignee: Conopco, Inc., Englewood Cliffs, NJ (US)

( * ) Notice: Subject to any disclaimer, the term of this patent is extended or adjusted under 35 U.S.C. 154(b) by 356 days.

(21) Appl. No.: 11/197,186

(22) Filed: Aug. 4, 2005

(65) Prior Publication Data

US 2006/0030510 A1 Feb. 9, 2006

(30) Foreign Application Priority Data

Aug. 4, 2004 (IN) .................................. 2004/0830

(51) Int. Cl.
*A61K 8/02* (2006.01)
(52) U.S. Cl. ..................................... 424/401
(58) Field of Classification Search .................. 424/401
See application file for complete search history.

(56) References Cited

U.S. PATENT DOCUMENTS

| 4,229,432 | A | * | 10/1980 | Geria ........................... 424/68 |
| 5,612,307 | A | | 3/1997 | Chambers et al. |
| 5,626,856 | A | * | 5/1997 | Berndt ........................ 424/401 |
| 5,833,965 | A | * | 11/1998 | Sun et al. ....................... 424/66 |
| 6,171,600 | B1 | | 1/2001 | Dahms |
| 6,268,322 | B1 | | 7/2001 | St. Lewis et al. |
| 6,306,806 | B1 | | 10/2001 | St. Lewis et al. |
| 2003/0152539 | A1 | | 8/2003 | Scavone et al. |

FOREIGN PATENT DOCUMENTS

| EP | 0 552 024 | 1/1993 |
| EP | 0 717 978 | 11/1995 |
| EP | 1 059 378 | 6/1999 |
| EP | 1 090 981 | 4/2001 |
| GB | 2 400 609 | 4/2003 |
| WO | 96/02225 | 2/1996 |
| WO | 96/41610 | 12/1996 |
| WO | 97/17938 | 5/1997 |
| WO | 01/28502 | 4/2001 |
| WO | 02/087516 | 11/2002 |
| WO | 2004/084844 | 10/2004 |
| WO | 2004/100906 | 11/2004 |
| WO | 2005044212 | 5/2005 |

OTHER PUBLICATIONS

International Search Report, PCT/EP2005/007990, mailed Oct. 31, 2005-3 pp.
GB Search Report, GB 0504245.2, dated Jun. 23, 2005-2 pp. Pursuant to MPEP § 2001.6(b) applicants bring the following *co-pending application* to the Examiner's attention: U.S. Appl. No. 10/980,478 filed Nov. 3, 2003, Krishnan, et al. Improved Detergent Compositions with Benefit Agents.

* cited by examiner

*Primary Examiner*—John R Hardee
(74) *Attorney, Agent, or Firm*—Alan A. Bornstein

(57) ABSTRACT

A rinse off liquid or gel cleansing composition comprising a continuous phase comprising one or more detergent actives and a dispersed phase comprising one or more hydrophobic materials, the dispersed phase comprising a water soluble or dispersible benefit agent which is sensitive to a detergent active and/or high pH, which benefit agent is dispersed in the hydrophobic material.

22 Claims, No Drawings

DETERGENT COMPOSITION WITH BENEFIT AGENTS

The present invention relates to incorporation of benefit agents that are incompatible with the detergent actives in a detergent liquid rinse-off cleansing composition. The benefit agent is dispersed in a hydrophobic phase as a solid, and/or as an aqueous solution/dispersion.

The invention thus provides for effective incorporation of benefit agents in various cosmetics and/or detergent compositions which degrade and/or affect the benefit characteristics of the benefit agent when in direct contact with the detergent active, or in high pH formulations where the high alkaline pH of the base formulation affects the benefit characteristics of the benefit agent.

Cosmetic compositions to deliver different benefit agents are prepared using different emulsifying systems and vehicles. These compositions are generally formulated as creams, lotions and other forms that are leave-on products. It has long been a desirable goal to deliver some of these benefit agents to the skin through a personal wash composition.

Delivery of benefit agents through a personal wash composition has proven to be much more difficult for a number of reasons. If the benefit agent interacts with the detergent active, then the benefit agent does not remain active in the final composition. There are certain other benefit agents that are unstable in the alkaline pH of the detergent composition, and it becomes difficult to keep them active in the formulation.

One way the above mentioned problem has been solved in the past is by spatially separating the detergent active system and the benefit agent by providing a dual-chamber package.

U.S. Pat. No. 5,612,307 for example teaches a dual-chamber package comprising separate surfactant and benefit agent stripe. The benefit agent in this prior art is a lipophilic benefit agent.

U.S. Pat. No. 6,306,806 discloses how to deposit a water-soluble benefit agent from a wash-off formulation. It discloses that by forming a water-in-oil emulsion of a water-soluble benefit agent in a hydrophobic emulsion and separately dispensing on to the substrate both the benefit agent containing emulsion and a surfactant containing composition from separate compartments, it has been possible to deposit greater amounts of both the water soluble benefit agent and of the oil forming the emulsion than otherwise achievable. The disclosure is restricted to water-soluble benefit agents like glycolic acid, lactic acid and salicylic acid, and does not disclose how to stabilise completely incompatible materials like antiperspirants, etc., where storage stability of the benefit agent along with a detergent active in a single compartment has not been possible.

U.S. 2003/0152539 A1 discloses an antisperspirant composition which is formulated based on the surprising finding that antiperspirant compositions containing petrolatum, a material that was previously known for inhibiting product wash-off and antiperspirant efficacy, can be formulated to deliver consumer perceived improvement in product wash-off and antiperspirant efficacy provided that the petrolatum is formulated at relatively low concentrations of from about 0.05% to about 0.95%. This is a leave-on product, and hence does not address the problem of stability of the benefit agent in a detergent composition, nor the deposition of the benefit agent through a wash-off product.

The above go to show the need for improving consumer attributes in various product formulations, both in terms of product form, as well as the efficacy in use/application.

It is however experienced that while benefit agents and their incorporation in cosmetic/detergent base formulations are useful to impart consumer perceivable end use benefits and add value to the product, it is important to ascertain the compatibility of the benefit agent desired to be incorporated in the base formulation. Otherwise, the presence of the benefit agent can degrade the product during storage and/or affect the usual properties of the benefit agent.

The above problems of incompatibility of benefit agents when in direct contact with cosmetic and detergent formulations would be further evident from the fact that very often various product forms, apart from loss in efficacy in deposition of the active benefit agent, also show problems of instability/degradation in the product appearance. This not only leads to loss of consumer appeal of the product, but can even render the product form not suitable for use.

It is thus well known that one needs to carefully select the benefit agent based on the basic cosmetic/detergent formulation in which the same is required to be incorporated, and also the manner in which the benefit agent is to be incorporated in the base formulation, keeping in view also the product form and use.

Thus, antiperspirant compositions which are usually low pH/mild formulations can involve direct incorporation of various forms of antiperspirant agents such as aluminum containing and/or zirconium containing salts, or materials such as aluminum halides, aluminum chlorohydrate, aluminum hydroxyhalides, zirconyl oxyhalides, zirconyl hydroxyhalides and mixtures thereof for controlling or inhibiting underarm perspiration, wetness and odor.

It is found that when such antiperspirant actives are directly incorporated in alkaline high pH or anionic base formulations, such as is usually in case of detergent formulations, the antiperspirant actives usually react and lose their identity in the product form. In particular, it is found that direct incorporation of aluminum chlorohydrate (ACH), a well-known antiperspirant active, in detergent formulation was not possible. This was because the same immediately reacts with the base formulation, and in the process results in precipitation of ACH.

Therefore, while a need exists for such antiperspirant to be introduced into detergent formulations, due to problems of incompatibility of the antiperspirant active with the detergent base or the alkaline pH of the formulation, the use of antiperspirant actives has been limited to only leave-on compositions. This necessarily is a clear limitation in the advantageous use of antiperspirants as benefit agents in detergent formulations.

Similar problems of incompatibility of benefit agents with certain cosmetic/detergent formulations leading to degradation of product is also noticed in direct incorporation of niacinamide, a skin whitening active, in soaps, especially in a high pH formulation. It is found that niacinamide, when incorporated in soap at levels beyond about 0.1%, interacts with the soap base resulting in undesirable coloration of the product. This is again a major problem, since use of niacinamide in soap could add value to the product. However, the coloration resulting from incorporation of niacinamide makes the product aesthetically unacceptable. Importantly, since for effective use of niacinamide in such formulations the same needs to be incorporated at levels beyond 0.1%, it's presence in soap formulations is avoided due to above discoloration and degradation of the product.

It would be clearly apparent from the above that incorporation of benefit agents into detergent formulations is advantageous, and may be required to add value to the product. It is difficult to formulate high pH or detergent formulations with direct incorporation of various benefit agents that are not compatible with the detergent base formulation, as they lead to either degradation of the product and/or loss of benefit actives/characteristics of the benefit agent, making it's incorporation of no use.

In our co-pending application 1166/Mum/2003, we have disclosed that rinse-off non-liquid cleansing compositions can be formulated wherein the detergent active sensitive or high pH sensitive water-soluble/dispersible benefit agent, when dispersed in a hydrophobic phase, can maintain the benefit agents storage-stable, and provide the desired benefit action during use. However this patent is restricted to solid formulations, and does not teach how to solve the problem of incompatibility of benefit agents and detergent actives in liquid/gel formulations.

It is especially difficult to incorporate the water-in-oil emulsion in a large detergent active liquid system, as the emulsion will not be stable. In the other literature document discussed above, U.S. Pat. No. 6,306,806, this resorts to physical separation of the two components by packaging them in separate compartments. US '806 discloses that the water soluble benefit agent can be added to the surfactant stripe, which goes to show that the benefit agents selected are not incompatible with the detergent active.

It has now been possible to incorporate detergent active sensitive/high pH sensitive benefit agents into detergent formulations in the form of liquid/gel and ensure that the benefit agent is stable during storage and effective in use.

It is thus the basic object of the present invention to be able to provide for incorporation of detergent active sensitive/high pH sensitive benefit agents which may not be compatible for direct incorporation in detergent rich or high pH liquid/gel base formulations. Thereby, on the one hand one may avoid problems of incompatibility and product degradation, and on the other also ensure the in-use efficacy of the benefit agent in the product.

Another object of the present invention is to be able to provide for formulations such as liquid/gel soap/non-soap detergent active formulations having detergent active sensitive/high pH sensitive benefit agents. In doing this, in the detergent composition we can not only incorporate such detergent active sensitive/pH sensitive incompatible benefit agents, but would also be able to release such benefit agent only when required during use/application of the formulation, maintaining desired efficacy.

Yet another object of the present invention is to be able to provide for detergent based rinse-off liquid/gel cleaning compositions comprising incompatible benefit agents selected from antiperspirant agents, skin lightening agents, perfuming agents, water softening agents, easy rinse off agents and malodor controlling benefit agents, which would enable storage stable incorporation of such actives, and maintain the desired efficacy in use/application of the product.

Thus according to a first aspect of the present invention, there is provided a rinse-off liquid/gel cleansing composition comprising a continuous phase of one or more detergent actives and a dispersed phase comprising one or more hydrophobic materials, wherein at least one detergent active sensitive/high pH sensitive water-soluble/dispersible benefit agent is dispersed in the said hydrophobic phase such as to maintain the same storage stable and of desired benefit action during use.

In accordance with a preferred aspect, there is provided a rinse-off liquid/gel cleansing composition comprising a continuous phase of one or more detergent active and a dispersed phase comprising one or more hydrophobic material, wherein at least one detergent active sensitive/high pH sensitive water-soluble/dispersible benefit agent is dispersed in the said hydrophobic phase as a solid and/or as an aqueous solution/dispersion such as to maintain the same storage stable and of desired benefit action during use.

According to a further preferred aspect of the present invention there is provided a water-in-oil emulsion system as a storage stable carrier of detergent active sensitive/high pH sensitive benefit agent comprising:
(i) an aqueous phase including at least one water soluble and/or dispersible benefit agent;
(ii) a hydrophobic protective carrier for said aqueous phase containing the benefit agent; and
(iii) an emulsifier/dispersant.

In accordance with a further preferred aspect of the invention there is provided a water-in-oil emulsion system as a storage stable carrier of benefit agents/actives in detergent formulations comprising:
a) a water-in-oil emulsion comprising:
i) an aqueous phase including at least one water soluble and/or dispersible detergent active sensitive/high pH sensitive benefit agent;
ii) a hydrophobic protective carrier for said aqueous phase containing the benefit agent; and
iii) an emulsifier; and
b) a detergent base formulation.

The above disclosed water-in-oil emulsion of the invention comprises 1% to 70% by wt. at least one detergent active sensitive/high pH sensitive water soluble and/or dispersible benefit agent; the hydrophobic protective carrier comprising 20% to 95% by wt.; and the emulsifier/dispersant in amount of 0.5% to 5% by wt. Importantly, if the benefit agent is water-soluble and incorporated in the selective water-in-oil emulsion, then the same can be added up to the solubility limit.

It is found that if the detergent active sensitive/pH sensitive benefit agent is provided dispersed in the hydrophobic phase so as to maintain the same storage stable and yet providing the desired benefit action during use, including the selective water-in-oil emulsion system, the same can be effectively stored free of any interaction in combination with any high pH reactive/detergent base media until the system is purposively subjected to any interactive actions, whereby the active is released from the system for the effective use/application. The invention therefore not only favours incorporation of the detergent active sensitive/pH sensitive benefit agent in high pH/detergent formulations, but essentially serves the dual purpose of maintaining desired non-reactive storage of the high pH/detergent base and the detergent active sensitive/pH sensitive benefit agent, as well as providing the desired efficacy during use, even in such adverse environments such as in the presence of detergent actives/high pH environments.

In accordance with another aspect of the present invention, there is provided a rinse off liquid/gel detergent cleansing composition comprising:
5% to 30% detergent active comprising a continuous phase; and
a dispersed phase comprising one or more hydrophobic materials, wherein at least one detergent active sensitive/high pH sensitive water-soluble/dispersible benefit agent is dispersed in the said hydrophobic phase so as to maintain the same storage stable and of desired benefit action during use.

In accordance with another aspect of the present invention there is provided a liquid/gel detergent composition comprising:
5% to 30% detergent active comprising a continuous phase;

a dispersed phase comprising one or more hydrophobic materials including a water-in-oil emulsion system as storage stable carrier of benefit agents comprising (i) an aqueous phase including at least one water soluble and/or dispersible benefit agent (ii) a hydrophobic protective carrier for said aqueous phase containing benefit agent, and (iii) an emulsifier/dispersant In accordance with yet another preferred aspect of the present invention, there is provided a liquid/gel detergent based composition comprising:

5% to 30% detergent active comprising a continuous alkaline phase;

a dispersed phase comprising one or more hydrophobic materials including a water-in-oil emulsion system as storage stable carrier of benefit agents/actives comprising (i) an aqueous phase including at least one water soluble and/or dispersible benefit agent (ii) a hydrophobic protective carrier, preferably oil based, with or without oil soluble additives for said aqueous phase containing benefit agent/active, and (iii) an emulsifier/dispersant.

In the above dispersed phase comprising the benefit agent carrier of the invention, the benefit agent can be selected from any conventional benefit agents such as antiperspirants, skin whitening agents, perfuming agents, water softening agents, rinse-off agents and malodor controlling benefit agents and other conventional benefit agents. In a preferred embodiment, preferred benefit agents are antiperspirants and skin whitening agents, especially antiperspirants. The dispersed phase in the composition is incorporated up to 20% by weight, and more preferably in the range 0.1% to 15% by weight.

In accordance with some preferred aspects of the invention, the benefit agent can be selectively detergent active sensitive aluminum chlorohydrate (ACH) as an antiperspirant, which when incorporated in the dispersed phase comprising one or more hydrophobic materials and incorporated in a detergent formulation would avoid the problems of ACH precipitation usually encountered upon direct incorporation of ACH in detergent formulations containing anionic actives, or in high pH media.

Thus, the formulation of the invention would serve as a protective carrier for the active in the detergent base involving incorporation of such antiperspirant in detergent formulations to add consumer attributes to the detergent product. Likewise, using the above dispersed phase comprising one or more hydrophobic materials, it is possible to incorporate other usually non-compatible pH sensitive benefit agents in detergent formulations such as niacinamide (a skin whitening aid), phosphate (a water softening benefit agent) water-soluble inorganic salts such as calcium and magnesium salts (as easy to rinse benefit aids), and Protein based actives (as malodor preventing agent).

Depending upon the purpose and the selected base formulation used, the active is selectively provided in amounts so as to be maintained in a storage stable state solubilized and/or dispersed in the oil phase.

It is particularly preferred to include thickeners in the range 0.2% to 2% in the formulation; suitable thickeners are categorized as cationic, nonionic, or anionic thickeners, and are selected to provide the desired viscosity. A few examples of the thickeners are hydroxypropyl guar gum, cationic guar gum, carbopol, and hydroxy ethyl cellulose.

In accordance with another aspect of the present invention, there is provided a process for manufacture of a rinse-off liquid cleansing composition comprising:
 i) providing a continuous phase of one or more detergent actives; and
 ii) providing a dispersed phase comprising one or more hydrophobic materials, wherein at least one detergent active sensitive/high pH sensitive water-soluble/dispersible benefit agent is dispersed in the hydrophobic phase so as to maintain the same storage stable and of desired benefit efficacy during use.

The above process of manufacture involving the continuous detergent phase and the dispersed phase including the benefit agent can be obtained following conventional process of liquid/gel detergent manufacture.

In accordance with another aspect of the present invention there is provided a process for the manufacture of liquid/gel detergent composition comprising:
 i) providing the selective hydrophobic carrier preferably oil based in the liquid state under conditions of emulsification with or without additional oil soluble actives and the emulsifier, and mixing the same in the temperature range of 20-95° C.;
 ii) adding the detergent active sensitive/pH sensitive benefit agent ingredient as a solution and/or a dispersion in oil;
 iii) mixing the hydrophobic carrier and emulsifier mix with the aqueous phase or powder to form the protective carrier for the benefit agent; and
 iv) mixing the above protective carrier with a base detergent formulation.

The present invention thus provides for a rinse-off liquid/gel cleansing composition comprising a continuous phase of one or more detergent actives and a dispersed phase comprising one or more hydrophobic materials, wherein at least one detergent active/high pH sensitive water-soluble/dispersible benefit agent is dispersed in the said hydrophobic phase so as to maintain the same storage stable and of desired benefit efficacy during use.

It is found that the problems of compatibility of some benefit agents, especially with the detergent formulations experienced in the art leading to instability of the product formed by direct incorporation of detergent active sensitive/pH sensitive benefit agents, can be avoided if the benefit agent is provided in the protective carrier system such as dispersed in a selective hydrophobic phase so as to maintain the same storage stable and of desired benefit efficacy during use.

Importantly, the dispersed phase having the benefit agent can be a water-in-oil emulsion/dispersion system in accordance with the present invention such that the benefit agent containing aqueous solution is maintained emulsified in oil or the benefit agent is dispersed in the oil. This on the one hand has the benefit of minimizing the interaction of the benefit agent with the surroundings/detergent base during storage, as there is an oil barrier between the benefit agent and the base formulation, and on the other hand maintaining desired efficacy of the benefit agent during use. It is only in use the oil barrier is selectively disturbed, and the benefit agent is supposed to leach out of its protective form and serve the purpose of the benefit agent in the formulation.

Advantageously, in the formulation of the invention the amount of the active in the dispersed phase having the benefit agent should be selectively provided based on the selected benefit agent and the required end use/application. Importantly, in situations where the benefit agent is required to be released at a later point of time, the dispersed phase is such that it would facilitate maintaining the active in its protected form within the hydrophobic carrier until it is desired to be exposed for the benefit during application.

The basic system in terms of the aqueous composition, emulsifier level and oil concentration will be same for all variants of benefit agents desired to be included in the system.

However, the amount of the active i.e. the benefit agent in the aqueous phase of the water-in-oil emulsion can be varied depending upon the extent of solubility or effective dispersibility of the active.

The detergent base formulation can be any conventional detergent formulation.

The dispersed phase would therefore essentially involve the hydrophobic carrier, which can be preferably selected from variety of oils including mineral oils, vegetable oils, silicone oils and synthetic oils. The oil may be a silicone compound, a hydrocarbon, or a mixture thereof. Exemplary silicone compounds include a polyalkyl siloxane, a polyaryl siloxane or a polyalkylaryl siloxane. Mixtures of these silicone compounds also is useful.

The oil also can be selected from mineral oil, petrolatum, sunflower seed oil, canola oil or mixtures thereof. Other exemplary hydrocarbon compounds that can be incorporated into the oil phase include, but are not limited to, a branched 1-decene oligomer, like 1-decene dimer or a polydecene.

The oil also optionally can comprise (1) an oil, such as jojoba oil, wheat germ oil or purcellin oil; or (2) a water insoluble emollient, such as, for example, an ester having at least about 10 carbon atoms, and preferably about 10 to about 32 carbon atoms.

Suitable esters include those comprising an aliphatic alcohol having about eight to about twenty carbon atoms and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight chained or branched. Preferably, the ester has a molecular wt. of less than about 500. Suitable esters therefore include, for example, but are not limited to:
  (a) aliphatic monohydric alcohol esters (e.g., isopropyl isostearate, cetyl acetate, cetyl stearate);
    myristyl propionate,
    isopropyl myristate,
    isopropyl palmitate,
    cetyl acetate,
    cetyl propionate,
    cetyl stearate,
  (b) aliphatic di- and tri-esters of polycarboxylic acids, (e.g., diisopropyl adipate);
  (c) aliphatic polyhydric alcohol esters (e.g., propylene glycol dipelargonate); and
  (d) aliphatic esters of aromatic acids, (e.g., $C_{12}$-$C_{15}$ alcohol esters of benzoic acid).

Most preferably petrolatum can serve as an effective hydrophobic carrier in the emulsion system. Preferably it is present at levels of at least 0.05%, preferably at least 0.1%, more preferably at least 0.5% and more preferably at least 1%. Preferably it is present at a level of no more than 5%, preferably no more than 3%, preferably no more than 2%, and in some instances possibly no more than 1%.

The emulsifier used in the water-in-oil emulsion can be selected from low HLB emulsifier that may comprise a silicon-free surfactant, or a blend of silicon-free surfactants, having an HLB value of about 10 or less (i.e., an HLB value of about 0.1 to about 10), an oil-soluble silicon-based surfactant, an oil-soluble polymeric surfactant, or mixtures thereof. Preferably, the silicon-free surfactant or surfactant blend has an HLB value of about 1 to about 7. To achieve the full advantage of the present invention, the silicon-free surfactant or surfactant blend has an HLB value of about 3 to about 6.

The term "oil-soluble" as used herein means a compound having a solubility of at least 0.1 g per 100 ml of oil phase to form a true solution.

The particularly preferred emulsifier used in the water-in-oil emulsion are selected from polysorbate esters (eg. sorbitan monooleate, sorbitan mono stearate etc.), soya sterol, ethoxylated soya sterol, triglycerol diisostearate, oleic acid monoglyceride, mixture of high molecular weight fatty acids and fatty acid salts and mixed esters consisting of pentaerythritol and fatty alcohol.

The benefit agents as mentioned above can be any conventional benefit agents presently available in the art. This can be selected from antiperspirants such as ACH, niacinamide (a skin lightening aid), water-soluble inorganic salts (easy rinse-off, water-softening benefit etc.) and protein based actives (as malodor preventing agent). The amount of actives can range up to 70% of the system and in case of emulsion system, the water soluble actives in the aqueous phase are up to their solubility limits.

EXAMPLES

The details of the invention its objects and advantages are explained hereunder in greater detail in relation to non-limiting exemplary illustrations hereunder.

Example 1

To demonstrate the stability of the antiperspirant active aluminum chlorohydrate (ACH) in presence of a detergent active when ACH is directly introduced in soap/non-soap detergent active bases the following experimentation was carried out.

Liquid body-wash formulations in which the detergent active is soap or non-soap is provided in Tables 1 and 2 respectively below. ACH was added as a 5% water-in-oil emulsion in both soap and non-soap formulations.

Preparation of the Water-in-Oil Emulsion
The dispersion or emulsification of ACH in petrolatum is prepared in the following way:
  1. Dissolving ACH in distilled water to form a 58% solution.
  2. Heating the petrolatum to 75° C. and when melted, dissolve the emulsifier (sorbitan monooleate/sorbitan monostearate) in it at the desired concentration (3%)
  3. While stirring the petrolatum, adding the 58% ACH solution at the desired amount. In the case of dispersion, ACH powder at the desired amount is slowly added.
  4. After addition of the active, continue mixing for 10 minutes and then cool the emulsion/dispersion to

TABLE 1

Soap based body wash formulation

| Ingredients | % Actives |
| --- | --- |
| Potassium soap | 16 |
| Polyols | 16 |
| Jaguar C13 | 0.6 |
| Chelating agents | 0.13 |
| Minor ingredients | 1.4 |
| Aluminum chlorohydrate | 2 |
| Sorbitan mono oleate | 0.1 |
| Sorbitan mono stearate | 0.05 |
| Petrolatum | 1.35 |
| Cetyl alcohol | 4 |
| Water | 58.37 |

TABLE 2

Non-soap based body wash formulation

| Ingredients | % Active |
|---|---|
| Sodium lauryl ethoxy sulphate | 16 |
| Jaguar C13 | 0.6 |
| Hydroxyethyl cellulose | 1.0 |
| Chelating agents | 0.13 |
| Minor ingredients | 1.4 |
| Aluminum chlorohydrate | 2 |
| Sorbitan mono-oleate | 0.1 |
| Sorbitan mono-stearate | 0.05 |
| Petrolatum | 1.35 |
| Cetyl Alcohol | 3.0 |
| Water | 74.37 |

Example 2

This illustration is directed to demonstrate the selective and advantageous application of the water-in-oil emulsion of the invention as a protective carrier for the ACH as an antiperspirant active in alkaline soap formulation or an anionic non-soap detergent formulation, thereby facilitating the benefit use/applications of ACH in soap/detergent formulation.

Example 2a

Preparation of Soap Solution

A 1% soap solution was prepared by dissolving the soap in distilled water at 70° C. and then cooling the solution to ambient temperature.

Example 2b

Preparation of Sodium Lauryl Ethoxy Sulphate (SLES) Solution.

A 16% SLES solution was prepared by dissolving SLES in distilled water.

Example 2c

Preparation of 100 mg ACH Incorporated Water-in-Oil Emulsion System in Accordance with the Invention To ascertain the stability of the ACH incorporated in the dispersed phase such as the water-in-oil emulsion in accordance with the invention, along with respective controls where the ACH was added directly into the soap/SLES solution was studied.

For the purpose of the above study two separate batches of the same soap solution of Example 2a was taken and in one batch 60 mg ACH was directly added and in the other batch 100 mg ACH was added through the water-in-oil emulsion system. The pH was measured using a pH meter and the turbidity using a turbidometer of the respective solutions containing the active ACH directly introduced (Control) and the active ACH in the water-in-oil emulsion, and the results are reproduced hereunder in Table 3.

TABLE 3

| Sample | pH | Turbidity |
|---|---|---|
| Soap solution | 10.14 | 205 |
| Soap + 60 mg ACH (Control) | 9.89 | 950 |
| Soap + 100 mg ACH through water-in-oil emulsion | 10.13 | 185 |

Similarly SLES body wash with 2% ACH added in the form of a water-in-oil emulsion was compared with 2% ACH added directly by determining the turbidity the results are reproduced hereunder in Table 4.

TABLE 4

| Sample | Turbidity |
|---|---|
| SLES solution | 1.9 |
| SLES + 2% ACH (Control) | >1000 |
| SLES + 2% ACH through water-in-oil emulsion | 13.8 |

It would be clearly apparent from the results in Table 3 and Table 4 above that when ACH as the benefit agent is introduced in the soap/SLES solution through the water-in-oil emulsion of the invention, the problem of precipitation of ACH in the alkaline phase or in presence of the detergent active is clearly avoided since the solution maintained a desired lower turbidity level. The above therefore clearly suggest the advantageous incorporation of active benefit agents in a protective form through water-in-oil emulsion which takes care of the required protection of the benefit agent in the presence of the detergent active or alkaline pH environments so that effective use of such actives under varying pH conditions can be achieved.

Both the control formulation and the formulation having ACH in a water-in-oil emulsion were tested by a batch of volunteers, and the dry feel and malodur generation was assessed. It was found that formulation containing the ACH in emulsion form in accordance with the invention showed superior antiperspirant characteristics.

Additional proof of the stability of ACH in our system is demonstrated in the example below.

Example 3

Under this example, 2.5 g of emulsion containing ACH was added to 100 g of water or 100 g of a 5% soap solution. In one case, there was no mixing and in the other case the water solution was stirred using a magnetic stirrer/overhead impeller. Water solution was drawn at desired time period and analyzed for aluminum concentration using inductively coupled plasma emission spectrometer (ICP). The results obtained are detailed hereunder in Table 5:

TABLE 5

| Sample | Time, hours | % ACH leached into water |
|---|---|---|
| Water - static | 2 | 0.45 |
| | 4 | 0.44 |
| | 6 | 0.45 |
| | 22 | 0.49 |
| Water - mixing | 2 | 0.51 |
| | 4 | 0.53 |
| | 6 | 0.64 |
| | 22 | 0.65 |

TABLE 5-continued

| Sample | Time, hours | % ACH leached into water |
|---|---|---|
| Soap - mixing | 2 | 0.85 |
| | 4 | 0.88 |
| | 6 | 0.96 |
| | 22 | 1.19 |

The data clearly shows that even under agitation, the amount of ACH leached into water from the emulsion is less than 2% of the total ACH.

The invention would thus enable high pH alkaline soap/non-soap base formulations to incorporate even detergent active/pH sensitive benefit agents avoiding problems of incompatibility and product degradation in use of such benefit agents experienced in the art as discussed above. Importantly, also the soap composition according to the invention and the selective dispersed phase of the active/benefit agent would enable incorporation of even incompatible detergent active sensitive/pH sensitive benefit agents/actives, which can be released only when required during use/application of the detergent formulation while maintaining storage stablility when not in use.

Example 4

Clinical Study to Determine the Effect on Malodour

A clinical study was conducted to determine the effectiveness of ACH containing body wash in reducing underarm malodour. The assessment was done by assessors, who are trained to rate the malodour on a scale of 0 to 5 where 0—no malodour and 5—high malodour.

Thirty-eight panellists (16 men and 22 women) with a high underarm malodour were selected for the exercise. Post bath with the body wash, assessors sniffed their (panellists') right and left underarms after 2, 4 and 8 hours and noted the malodour reading as per their training on assessing malodour. Panellists used each product in a randomized order for seven days. Their readings were taken on third, fifth and seventh day of usage. Half the panellists used control in first week and others used experimental.

The body wash formulation used in the study is provided in Table 6. The results are presented in Table 7.

TABLE 6

| Ingredients (% by weight) | Example 4a | Example 4b | Example 4c |
|---|---|---|---|
| Potassium soap | 20 | 20 | 16 |
| Antibacterials (mixture of trichlorocabanilide, triclosan) | — | 0.2 | 0.2 |
| Aluminum chlorohydrate as a water-in-oil emulsion# | — | — | 2 |
| Sorbitan mono oleate | — | — | 0.2 |
| Sorbitan mono stearate | — | — | 0.1 |
| Petrolatum | — | — | 1.35 |
| Conventional ingredients | 2 | 1.8 | 2.15 |
| Polyols, Cetyl alcohol, Water | 78 | 78 | 78 |

The ACH emulsion was prepared using sorbitan monooleate, sorbitan monostearate, petrolatum.

TABLE 7

| Average Malodour Scores of all the panellists | | | |
|---|---|---|---|
| Duration | Example 4a | Example 4b | Example 4c |
| 2 hour | 0.7 | 0.9** | 0.4**** |
| 4 hour | 1.0 | 1.3*** | 0.8**** |
| 8 hour | 1.5 | 1.5 NS | 0.9**** |

NS—Not significant;
**:—95% significance;
***:—99% significance;
****:—99.9% significance The body wash containing only antibacterials do not show any benefit over the control (in fact control is better at 2 & 4 hours) while the ACH containing body wash shows a significant benefit in reducing underarm malodour over control.

The invention claimed is:

1. A rinse off liquid or gel cleansing composition comprising a continuous phase comprising one or more detergent actives and a dispersed phase comprising one or more hydrophobic materials, the dispersed phase comprising a benefit agent which is an antiperspirant capable of dissolving in water, which is sensitive to a detergent active or high pH or both, wherein the benefit agent is dispersed in the hydrophobic material and wherein the dispersed phase is in the form of a water-in-oil emulsion and comprises an emulsifier or dispersant.

2. A rinse off liquid or gel cleansing composition according to claim 1, wherein the hydrophobic material is selected from mineral oils, vegetable oils, silicone oils and synthetic oils, and mixtures thereof.

3. A rinse off liquid or gel cleansing composition according to claim 1, wherein the hydrophobic material comprises petrolatum.

4. A rinse off liquid or gel cleansing composition according to claim 3, wherein the petrolatum is present at a level of 0.05% to 5%.

5. A rinse off liquid or gel cleansing composition according to claim 1, wherein the dispersed benefit agent is in the form of a solid, or an aqueous solution or dispersion.

6. A rinse off liquid or gel cleansing composition according to claim 1, wherein the dispersed phase comprises 1% to 70% by weight of a benefit agent, the hydrophobic material comprises 20% to 95% by weight, and the emulsifier or dispersant comprises 0.5% to 5% by weight.

7. A rinse off liquid or gel cleansing composition according to claim 1, wherein the benefit agent is included in the water-in-oil emulsion up to the solubility limit.

8. A rinse off liquid or gel cleansing composition according to claim 1, wherein the composition comprises 5% to 30% detergent active.

9. A rinse off liquid or gel cleansing composition according to claim 1, wherein the hydrophobic material is oil based.

10. A rinse off liquid or gel cleansing composition according to claim 1, wherein the hydrophobic material comprises oil-soluble additives.

11. A rinse off liquid or gel cleansing composition according to claim 1, wherein the continuous phase is alkaline.

12. A rinse off liquid or gel cleansing composition according to claim 1, wherein the benefit agent is aluminium chlorohydrate.

13. A rinse off liquid or gel cleansing composition according to claim 1, wherein the dispersed phase comprises 0.1% to 20% by weight of the composition.

14. A rinse off liquid or gel cleansing composition according to claim 1, wherein the composition additionally comprises 0.2% to 2% by weight of a thickener.

15. A rinse off liquid or gel cleansing composition according to claim 14, wherein the thickener is cationic, non-ionic or anionic.

16. A rinse off liquid or gel cleansing composition according to claim 1, wherein the hydrophobic material is selected from mineral oils, vegetable oils, silicone oils and synthetic oils, and mixtures thereof.

17. A rinse off liquid or gel cleansing composition according to claim 1, wherein the composition comprises an emulsifier having an HLB value of 10 or less.

18. A rinse off liquid or gel cleansing composition according to claim 17, wherein the emulsifier is a silicon-free surfactant, an oil-soluble silicon based surfactant, an oil-soluble polymeric surfactant, or mixtures thereof.

19. A rinse off liquid or gel cleansing composition according to claim 17, wherein the emulsifier has an HLB value of between 3 and 6.

20. A rinse off liquid or gel cleansing composition according to claim 1, wherein the composition is soap or non-soap anionic surfactant based.

21. A process for manufacture of a liquid/gel detergent composition comprising:
   i) mixing a liquid hydrophobic material and an emulsifier or dispersant to form a preblend or emulsion;
   ii) adding an aqueous solution, a dispersion in oil or a powder to the product of step (i) wherein the solution, dispersion or powder contains a detergent active sensitive or pH sensitive benefit agent which is an antiperspirant capable of dissolving in water;
   iii) mixing the product of step (ii) to form a protective carrier for the benefit agent; and
   iv) mixing the product step (iii) with a base detergent formulation for form a continuous phase containing detergent actives wherein the dispersed phase is in the form of a water-in-oil emulsion.

22. The process of claim 21 wherein the mixing step (iii) is carried out at a temperature in the range of 20° C. to 95° C.

* * * * *